(12) United States Patent
Parenti et al.

(10) Patent No.: US 6,720,305 B1
(45) Date of Patent: Apr. 13, 2004

(54) INJECTABLE FORMULATIONS CONTAINING RAMOPLANIN

(75) Inventors: Francesco Parenti, Lainate (IT); Gianpaolo Candiani, Gorgonzola (IT); Romeo Ciabatti, Novate Milanese (IT); Marco Cavaleri, Saronno (IT)

(73) Assignee: Vicuron Pharmaceuticals Inc., King of Prussia, PA (US)

( * ) Notice: Subject to any disclaimer, the term of this patent is extended or adjusted under 35 U.S.C. 154(b) by 0 days.

(21) Appl. No.: 09/744,247

(22) PCT Filed: Jul. 19, 1999

(86) PCT No.: PCT/EP99/05137

§ 371 (c)(1),
(2), (4) Date: Jan. 30, 2001

(87) PCT Pub. No.: WO00/06119

PCT Pub. Date: Feb. 10, 2000

(30) Foreign Application Priority Data

Jul. 30, 1998 (EP) .............................................. 98114368

(51) Int. Cl.[7] .............................................. A61K 38/12
(52) U.S. Cl. ........................ 514/11; 514/13; 530/317; 530/326; 424/450
(58) Field of Search ..................... 514/11, 13; 530/317, 530/326; 424/450

(56) References Cited

U.S. PATENT DOCUMENTS

| | | | | |
|---|---|---|---|---|
| 4,990,337 A | * | 2/1991 | Kurihara et al. | 424/427 |
| 5,225,212 A | * | 7/1993 | Martin et al. | 424/450 |
| 5,514,670 A | * | 5/1996 | Friedman et al. | 514/2 |
| 5,646,109 A | * | 7/1997 | Owen et al. | 514/2 |
| 5,662,930 A | * | 9/1997 | Ahl et al. | 424/450 |
| 5,688,761 A | * | 11/1997 | Owen et al. | 514/2 |
| 5,885,613 A | * | 3/1999 | Holland et al. | 424/450 |
| 5,891,846 A | * | 4/1999 | Ishida et al. | 514/11 |
| 5,916,588 A | * | 6/1999 | Popescu et al. | 424/450 |
| 5,968,899 A | * | 10/1999 | Sekine et al. | 514/12 |
| 2002/0099067 A1 | * | 7/2002 | Posanski | 514/291 |

FOREIGN PATENT DOCUMENTS

| | | |
|---|---|---|
| EP | 0 318 680 | 6/1989 |
| EP | 0 321 696 | 6/1989 |
| EP | 0 337 203 | 10/1989 |
| GB | 2 045 231 | 10/1980 |
| WO | WO 95/21636 | 8/1995 |

OTHER PUBLICATIONS

Romeo, B. (Program and Abstracts of the Interscience Conference on Antimicrobial Agents and Chemotherapy, (1993) vol. 33, No. 0, pp. 200. Meeting Info.: 33rd Interscience Conference on Antimicrobial Agents and Chemotherapy New Orleans, Louisiana, USA.*

Romeo, B (Microbial Ecology in Health and Disease, (1992) vol. 2, No. 6, pp. XX. Meeting Info.: XVII International Congress on Microbial Ecology and Disease Helsinki, Finland Aug. 28–29, 1992).*

Espersen, F., Curr. Opinion Anti–Infect Invest Drugs 1(1) 78–86, 1999.*

* cited by examiner

Primary Examiner—Christopher S. F. Low
Assistant Examiner—David Lukton
(74) Attorney, Agent, or Firm—Oblon, Spivak, McClelland, Maier & Neustadt, P.C.

(57) ABSTRACT

The present invention relates to a pharmaceutical composition for intravenous administration that contains ramoplanin or a member of the ramoplanin family.

44 Claims, No Drawings

INJECTABLE FORMULATIONS CONTAINING RAMOPLANIN

The present invention relates to a new injectable formulation of ramoplanin or a compound of the ramoplanin family. More particularly, the injectable formulations of the invention are particularly suitable for intravenous (i.v.) administration.

Ramoplanin (INN) is a known member of the cyclic peptide antibiotics more precisely known as glycolipodepsipeptides which has been described in U.S. Pat. No. 4,303,646 and U.S. Pat. No. 4,328,316. Originally it has been named antibiotic A 16686. It is a complex substance whose separate factors $A_1$, $A_2$ and $A_3$ have been described in U.S. Pat. No. 4,427,656.

Ramoplanin factors $A'_1$, $A'_2$ and $A'_3$ have been described in EP-B-318680, the aglycones of any of the above factors have been described in U.S. Pat. No. 5,491,128 while the tetrahydrogenated derivatives of any of the above factors have been described in U.S. Pat. No. 5,108,988. A method for selectively increasing the ratio of single major components $A_2$ $A_3$ is described in EP 0259780. All the above mentioned patents are incorporated herein by reference.

The structure of ramoplanin and its factors and derivatives have been described in several articles and publications, see R. Ciabatti et al., J. Antib. 1989, 254–267, J. K. Kettenring et al., J. Antob 1989, 268–275, R. Ciabatti and B. Cavalleri, Bioactive Metabolites from Microorganisms, Elsevier Science Publishers, 1989, 205–219 and M. Kurz and W. Guba, Biochemistry 1996, 35, 12570–124575.

R' represents alpha-D-mannopyranosyl or s-o-alpha-D-mannopyranosyl-alpha-D-mannopyranosyl.

N. J. Skelton et al. in J. Am. Chem. Soc. 1991, 113, 7522–7530 describe another member of this family, which they call Ramoplanose.

These compounds can be represented by the following formula (Formula I):

FORMULA I

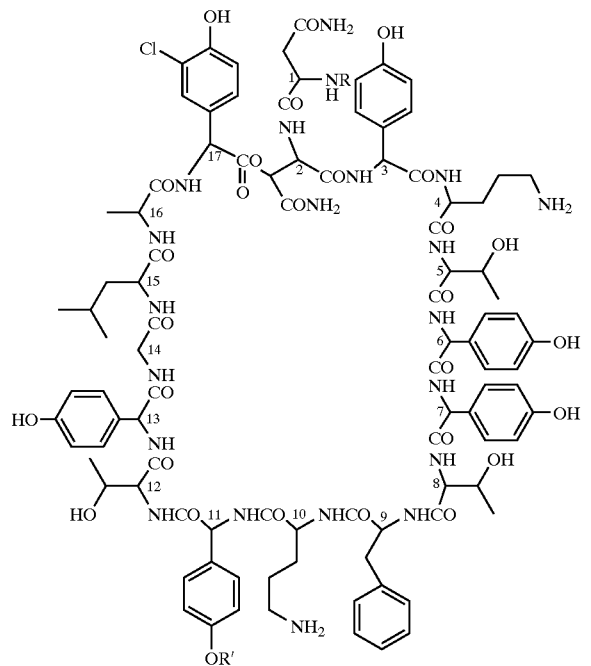

wherein:
R represents —CO—CH=CH—CH=CH—CH$_2$—CH$_2$—CH$_3$,

—CO—CH=CH—CH=CH—CH$_2$—CH (CH$_3$)$_2$,
—CO—CH=CH—CH=CH—CH$_2$—CH$_2$—CH (CH$_3$)$_2$,
—CO—CH$_2$—CH$_2$—CH$_2$—CH$_2$—CH$_2$—CH$_2$—CH$_3$,
—CO—CH$_2$—CH$_2$—CH$_2$—CH$_2$—CH$_2$—CH (CH$_3$)$_2$
or
—CO—CH$_2$—CH$_2$—CH$_2$—CH$_2$—CH$_2$—CH$_2$—CH (CH$_3$)$_2$

R' represents alpha-D-mannopyranosyl or 2-O-alpha-D-mannopyranosyl-alpha-D-mannopyranosil, or R' represents 2,3-O-di[alpha-D-mannopyranosyl]-D-mannopyranosyl when R represents —CO—CH=CH—CH=CH—CH$_2$—CH(CH$_3$)$_2$, a pharmaceutically acceptable acid addition salt thereof, or a mixture thereof in any proportion.

The configuration of the double bonds of the unsaturated moieties reported above in the definition of R have been found to be 2 (E) or cis and 4 (Z) or trans in the literature reported above.

The following table specifies the meanings for R and R' of the single factors or derivatives with reference to the above formula:

| Factor | R | R' |
|---|---|---|
| $A_1$ | —CO—CH=CH—CH=CH—CH$_2$—CH$_2$—CH$_3$ | 2-O-alpha-D-mannopyranosyl-alpha-D-mannopyranosyl |
| $A_2$ | —CO—CH=CH—CH=CH—CH$_2$—CH(CH$_3$)$_2$ | 2-O-alpha-D-mannopyranosyl-alpha-D-mannopyranosyl |
| $A_3$ | —CO—CH=CH—CH=CH—CH$_2$—CH$_2$—CH(CH$_3$)$_2$ | 2-O-alpha-D-mannopyranosyl-alpha-D-mannopyranosyl |
| $A'_1$ | —CO—CH=CH—CH=CH—CH$_2$—CH$_2$—CH$_3$ | Alpha-D-mannopyranosyl |
| $A'_2$ | —CO—CH=CH—CH=CH—CH$_2$—CH(CH$_3$)$_2$ | Alpha-D-mannopyranosyl |
| $A'_3$ | —CO—CH=CH—CH=CH—CH$_2$—CH$_2$—CH(CH$_3$)$_2$ | Alpha-D-mannopyranosyl |

The aglycones correspond to the compounds reported above wherein R' represents hydrogen while the tetrahydrogenate derivatives correspond to the compounds reported above wherein the mojety R is fully hydrogenated.

Ramoplanose is reported to correspond to "factor $A_2$" wherein R' represents 2,3-O-di[alpha-D-mannopyranosyl]-D-mannopyranosyl.

In the following description and claims, the term "ramoplanin" refer to a ramoplanin complex wherein factor $A_2$ is the major component, with a small amounts of factors $A'_2$, $A_1$, $A'_1$, $A_3$, $A'_3$ and other related substances accounting for the remainder of this active ingredient.

Particularly preferred is "ramoplanin" wherein factor $A_2$ represents at least, 75% of the active ingredient.

"A member of the ramoplanin family" refers to any of the compounds reported above that are represented by Formula I, any salt or any mixture thereof in any proportion.

Ramoplanin as well as any members of the ramoplanin family are unsuitable for i.v. administration because of drawbacks such as swelling and progressive necrotization at the site of injection, and haemolysis as revealed by urine discoloration.

The formulations of the invention contain ramoplanin or a member of the ramoplanin family in admixture with a fat emulsion product for intravenous administration.

In general, for i.v. administration purposes according to this invention, it is suitable to utilize liquid compositions wherein ramoplanin or a member of ramoplanin family is present in concentration from 1 to 20 mg/ml, preferably, from 1.5 to 15 mg/ml, most preferably, from about 3 to about 5 mg/ml.

In the current description and claims the expressions "fat emulsion product for intravenous injection" or "fat emulsion product" identify any of those fat emulsion products suitable for intravenous administration via a peripheral vein or by a central venous infusion that are currently used mainly to assure calories intake when parenteral nutrition is required. Examples of these substances are for instance reported in US Pharmacopeia, Martindale, The Extra Pharmacopeia (31$^{st}$ edition, 1996, page 1377) or VIDAL 1996, page 814. The above expressions include also those emulsions used as colloidal drug carriers, examples of which are reported in the book "Submicron Emulsions in Drug Targeting and Delivery" edited by S. Benita, Horwood Academic Publishers, 1998, at pages 119–122. All above cited publications are incorpored hereby by reference.

The above said fat emulsion products are largely based on an oil phase stabilized by emulsifiers, like phospholipids, poloxamers or other polyoxyethylene derivatives such as, for instance, polysorbates or polyoxyethylene castor oil.

Typically, a fat emulsion product suitable for preparing a formulation of the invention comprises an oil phase (usually 2–40%, preferably, 5–25% weight/vol), preferably consisting of vegetable oils such as soybean oil, safflower oil and cottonseed oil, emulsifiers (usually 0.2–5%, preferably, 0.5–2% weight/vol), preferably based on phospholipids of egg source such as egg lecithin or soybean lecithin, and additives as osmotic agents such as glycerol, sorbitol and xylitol.

These fat emulsion products, as commercially available, are emulsions comprising the above mentioned oil phase, emulsifiers and additives dispersed in water for injection and the oil phase is generally present in the emulsion in a percentage (weight/vol) of 5 to 25%. For preparing the i.v. administrable formulation of this invention, the fat emulsion product may be used as such or diluted with saline or water for injection added with an osmotic agent (eg. glucose) to decrease the oil phase concentration to a lower value and, at the same time, maintaining the desired osmolarity.

In general, if the concentration of ramoplanin or a member of ramoplanin family in the formulation is low, it is possible to lower the percentage of the oil phase in said i.v. formulation.

For instance, with ramoplanin concentrations of about 10 mg/ml, the percentage of the oil phase in the i.v. formulations of the invention may range between 4 to 40% (weight/vol) although are preferred those i.v. fat emulsions wherein the oil phase is between 4 and 25%, and, more preferably, between 8 and 18%, with the range 8–10% being currently the most preferred concentration.

With ramoplanin concentrations of about 1 mg/m the percentage of the oil phase in the i.v. formulation can be lowered to a range between 0.2 and 10% (weight/vol).

Generally, the osmolarity of the final i.v. formulation is between 250 and 300 mOsm/L, while the value of the pH must be compatible with the stability of ramoplanin (or a member of the ramoplanin family), and, therefore, usually, it should not be higher than 8.

As known in the art, particle size of the emulsion needs to be controlled for a proper i.v. administration, and this is accomplished through the conventional preparation and final formulation procedures.

Examples of fat emulsion products that can be conveniently used according to the present invention are those listed at page 120 of the above cited book: "Submicron Emulsion in Drug Targeting and Delivery" where the oil phase consists of soybean oil, cottonseed oil, safflower oil or mixture thereof.

Soybean oil, cottonseed oil and safflower oil contain long chain fatty acids comprising mainly linoleic acid, oleic acid, palmitic acid, linolenic acid and stearic acid, essentially in the form of triglycerides.

Soybean oil, cottonseed oil and safflower oil can be totally or in part substituted by any mixtures of the above fatty acids in the form of triglycerides having a percent (weight/weight) composition substantially similar to that of the above oils or their mixtures. Moreover, part of the above mentioned vegetable oils or long chain fatty acids triglycerides may be substituted by medium chain ($C_6$–$C_{12}$) triglycerides.

Typically, the fat emulsion product used for the preparation of the i.v. formulations of this invention contains an oil phase in a range from 2 to 40 percent (weight/vol), preferably, from 5 to 25 percent, more preferably from 7 to 20 percent, emulsifiers) in a range from 0.2 to 5 percent (weight/vol), preferably, from 0.6 to 2 percent more preferably from 0.5 to 1.5 percent, and the additive is in an amount suitable to control osmolarity, preferably, in a range from 1.5 to 5 percent (weight/vol), more preferably preferably from 2 to 3 percent.

In said oil phase consisting of soybean oil, cottonseed oil or safflower oil or mixture thereof, or in the fatty acids mixtures which may substitute totally or in part the above oils, the fatty acids triglycerides are usually present in the following percent (weight/weight) proportion indicated between brackets: linoleic acid (40–70%), oleic acid (15–30%), palmitic acid (5–15%), linolenic acid (3–12%), stearic acid (2–6%).

As indicated above, for the preparation of the i.v. formulations of this invention, the above said fat emulsion products are used as such or are diluted in a isoosmotic water solution for injection to a concentration of the oil phase in the final composition that is at least 0.2% (weight/vol), normally, depending on the concentration of ramoplain or a member of ramoplanin family which is present in the final composition.

According to a preferred embodiment of this invention, those fat emulsion products that are currently available under the trade names Intralipid®, Liposyn® and Lipofundin® may be utilized. For instance, Intralipid® (Kabi Vitrum/Pharmacia) and Liposyn® II and Liposyn® III (Abbott), have composition and physico-chemical properties as reported below:

TABLE I

Composition and characteristics of Various Intravenous Fat Emulsions

| Components or Characteristics | Intralipid ® (Kabi-Vitrum/Pharmacia) | | Liposyn ® II (Abbott) | | Liposyn ® III (Abbott) | |
|---|---|---|---|---|---|---|
| Soybean oil (w/vol) | 10% | 20% | 5% | 10% | 10% | 20% |
| Safflower oil (w/vol) | — | — | 5% | 10% | — | — |
| Egg yolk phospholipids (w/vol) | 1.2% | 1.2% | 1.2% | 1.2% | 1.2% | 1.2% |
| Glycerol (w/vol) | 2.25% | 2.25% | 2.5% | 2.5% | 2.5% | 2.5% |
| Water for injection | QS | QS | QS | QS | QS | QS |
| Fatty acids composition of vegetable oils (w/w) | | | | | | |
| Linoleic acid | | 50% | | 65.8% | | 54.5 |
| Oleic acid | | 26% | | 17.7% | | 22.4 |
| Palmitic acid | | 10% | | 8.8% | | 10.5 |
| Linolenic acid | | 9% | | 4.2% | | 8.3% |
| Stearic acid | | 3.5% | | 3.4% | | 4.2% |
| Osmolarity (mOsm/L) | 260 | 268 | 276 | 258 | 284 | 292 |
| Approximate pH | 8 | 8 | 8 | 8.3 | 8.3 | 8.3 |
| Fat particle size ($\mu$m) | 0.5 | 0.5 | 0.4 | 0.4 | 0.4 | 0.4 |
| Caloric value (cal/ml) | 1.1 | 2.0 | 1.1 | 2.0 | 1.1 | 2.0 |
| Size (ml) | 50, 100 250, 500 | 50, 100 250, 500 | 25, 50 100, 200 500 | 25, 50 200, 500 | 100, 200 500 | 200, 500 |

As stated above, in the formulations according to this invention ramoplanin or a member of the ramoplanin family as defined above is generally present in the compositions of the invention in an amount of 1 to 20 mg/ml, with a range of 1.5 to 15 mg/ml being currently preferred, and a range from about 3 to about 5 mg/ml being the most preferred one.

Typically, the composition of the invention is a composition wherein the oil phase in the final fat emulsion is between 0.2 and 40% (weight/vol), with a range 4–25% being preferred, a range 8–18% being more preferred and with the range 8–10% being currently most preferred. However, as mentioned above, the proportion of the oil phase may be adjusted to the one of the antibiotic and to lower amounts of ramoplanin may correspond lower amounts of oil phase in the composition Experiments with representative examples of the compositions of the invention have shown a good tolerability at the site of injection, in particular in comparison with the effects of conventional i.v. preparations of the same active principle.

The results of a first set of tolerability studies of representative examples of formulations of the invention in rats at a concentration of ramoplanin of 10 mg/ml (dose 20 mg/kg, administration volume 2 mg/kg), in comparison with a conventional i.v. formulation of the same active principle, are summarized in the following.

More particularly, ramoplanin in a conventional aqueous vehicle (0.9% saline) or in the formulations of the invention wherein the proportion of the oil phase in the total formulation is between 2 and 8% (weight/vol) is administered to rats (3–5 animal/group) at a dose of 20 mg/kg (drug concentration 10 mg/ml). The administered volume is 2 ml/kg, according to the animal weight on the day of administration, and the injection speed is 0.1 ml/sec. The intravenous administration is into the caudal vein. Treatment are planned for three days at 24 hours intervals. Control rats receive either 0.9% saline or an equivalent volume of Intralipid® 10%. Behavior and physical appearance are observed frequently the day of dosing. Urine appearance is also recording within 3 h after each daily treatment. Rats are sacrificed 24 h after the last treatment. The results of these experiments are summarized in Table II.

TABLE II

Urine appearance, gross pathology at the injection site and clinical observations of rats treated with ramoplanin formulated with Intralipid ® or in a conventional aqueous vehicle (0.9% saline)

| Groups | No. Animals | Saline (w/vol) | Intralipid ® (a) (w/vol) | Ramoplanin concentration | Urine Appearance (b) | Gross Pathology at the injection site (c) |
|---|---|---|---|---|---|---|
| A | 3 | 0.9% | — | — | Normal | Normal |
| B | 4 | 0.9% | — | 10 mg/ml (d) | Red-brown | Dark, discolored tails |
| C | 3 | — | 10% | — | Normal | Normal |
| D | 5 | — | 8% | 10 mg/ml | Normal | Normal |
| E | 5 | — | 4% | 10 mg/ml | Normal | Normal |
| F | 5 | — | 2% | 10 mg/ml | Red-brown | Dark, discolored tails |

(a) In water for injection, q.s. 100%
(b) Visual examination performed within 2–3 h after each scheduled treatment
(c) Examinations performed at the end of the three scheduled treatments
(d) Corresponding to a dose of 20 mg/kg Treatments with ramoplanin at a concentration of 10 mg/ml in conventional aqueous vehicle or in formulation with 2% (weight/vol) of oil phase caused darkness or discoloration at the injection site (tail). In contrast, treatment with the formulations of the invention wherein the oil phase was 4% (weight/vol) or higher was well tolerated. Tails did not show any sign of necrotic inflammation.

After the immediate postdose period of each treatment (3 h) with the formulations of the invention wherein the oil phase was 4% (weight/vol) or higher, the urine appeared light straw to dark yellow in colour. In contrast, rats given a 2% (weight/vol) oil phase formulation or ramoplanin in conventional aqueous vehicle developed red to red-brown urine, within the same postdose period.

A second set of experiments was carried out to determine tolerability of the formulation of the invention according to the same procedure described above but administering a dose corresponding to 10 mg/kg instead of 20 mg/kg to several groups of three rats for 3 days at 24 hours intervals. The concentration of ramoplanin in the formulation was 1 mg/ml instead 10 mg/ml and the volume of the formulation administered to each rat was 10 mg/kg instead of 2 mg/kg. The Intralipid® fat emulsion product was added in several different proportion as represented in the following Table III where the same parameters considered in Table II are reported. The rats were killed 24 h after the last treatment. Table III. Urine appearance, gross pathology at the injection site and clinical observations of rats treated with ramoplanin formulated with Intralipid® or in a conventional aqueous vehicle (0.9%)

TABLE III

Urine appearance, gross pathology at the injection site and clinical observations of rats treated with ramoplanin formulated with Intralipid ® or in a conventional aqueous vehicle (0.9% saline)

| Groups | No. Animals | Saline (w/vol) | Intra- lipid ® (w/vol) (a) | Ramoplanin concen- tration | Urine Appear- ance (b) | Gross Pathology at the injection site (c) |
|---|---|---|---|---|---|---|
| A | 3 | 0.9% | — | 1 mg/ml (d) | Red- brown | Dark tails (2/3) |
| B | 3 | — | 9% | 1 mg/ml | Normal | Normal |
| C | 3 | — | 1% | | Normal | Normal |
| D | 3 | — | 0.5% | 1 mg/ml | Normal | Normal |
| E | 3 | — | 0.2% | 1 mg/ml | Normal | Normal |
| F | 3 | — | 0.1% | 1 mg/ml | Red- brown | Discolored tails (3/3) |

(a) In water for injection, q.s. 100%
(b) Visual examination performed within 3 h after each scheduled treatment
(c) Examinations performed at the end of the three scheduled treatments
(d) Corresponding to a dose of 10 mg/kg The above data show that ramoplanin at a concentration of 1 mg/ml can be safely administered intravenously to experimental animals at a dosage of 10 mg/kg when the drug is appropriately formulated according to this invention in emulsion compositions containing Intralipid® in such amount that the oil phase is at least 0.2 per cent (w/vol) of the total formulation.

The effectiveness of representative examples of the compositions of the invention in experimental animal models can be demonstrated in several acute septicemia experiments in immunocompetent or neutropenic mice and in experiments of endocarditis and pneumococcal lobar pneumonia in rats.

Experimental septicemia is induced by inoculating intraperitoneally (5–6 animal/dose/treatment group) a bacterial suspension of either a clinical isolate of a methicillin resistant staphylococcus (Staph. aureus L613) or streptococcus strain (Strep. pneumonia L 44) in immunocompetent mice or a clinically isolated glycopeptide resistant enterococcus strain (Ent. faecium L569) in neutropenic mice. Immunocompetent mice are male and female $CD_1$ mice (Charles River Labs., Calco, Italy) weighting 18–22 g while neutropenic mice are 6–8 weeks old female NMRI mice (Iffa Credo, France).

Untreated animals die within 24–72 h after infection. Antibiotic treatment begins within 10 min after injection. Ramoplanin at various concentration is administered intravenously in conventional aqueous vehicle or in the formulation of the invention in 8% (weight/vol) oil phase fat emulsion. Gentamicin, vancomycin, teicoplanin and rifampicin can be included as comparator drugs. The 50% effective dose ($ED_{50}$) and 95% confidence limits are calculated by the Spearman-Karber method from the percentage of animal surviving at day 10.

The animals are treated twice, first 10 min from infection and then 24 h later.

When the gentamicin or vancomycin are employed as comparators, they are administered subcutaneously and second shot is given 5 h after infection. Rifampicin and teicoplanin are administered subcutaneously in single dose 10 min after infection.

Results of experiments conducted as described above are reported in the following table:

TABLE IV $ED_{50}$ of ramoplanin in experimental septicemia in mice.

| Strain (animal) | Formulation | $ED_{50}$ mg/kg/dose (95% confidence limits) |
|---|---|---|
| VanA Ent. faecium L 569 (neutropenic mice)[a] | Ramoplanin in 0.9% saline Ramoplanin in 8% Intralipid ® | 5.1 (d) 1.7 (1.4–2.0) |
| Staph. aureus L 613 (immunocompetent mice)[b] | Ramoplanin in 0.9% saline Ramoplanin in 8% intralipid ® | 4.3 (3.1–6.0) 5.1 (3.9–6.5) |
| Strep. pneumonia L 44 (immunocompetent mice)[c] | Ramoplanin in 0.9% saline Ramoplanin in 8% Intralipid ® | 0.06 (d) 0.06 (d) |

[a]$ED_{50}$ of comparators were as follows: gentamicin 50.6 (37.3–68.7), rifampicin 1.2 (0.9–1.5), vancomycin > 90%.
[b]$ED_{50}$ of comparator (teicoplanin) was 5.4 (4.3–6.9).
[c]$ED_{50}$ of comparator (teicoplanin) was 0.79 (0.65–0.96).
(d) Confidence limit could not be calculated because survival was either 0 or 100% in each treatment group.

Endocarditis experiments can be performed in experiment animals (rats) with isolates of staphylococci or enterococci. A polyethylene catheter is inserted through the aortic valve into the left ventricle of the animal via the right carotid artery. Two days later, the animals are infected i.v. Treatment begins the day after infection and continues for a total of 5 days. Surviving animals are killed on day 7 after infection. The hearts of all animals are homogenized and processed to determine bacterial load, that is expected to be substantially reduced in the treatment group receiving the formulations of the invention, in comparison with untreated controls.

Pneumonia experiments can be performed in both immunocompetent and neutropenic rats with e.g. a clinically isolated penicillin-resistant Strep. pneumoniae strain. Anesthetized animals are infected by surgical intrabronchial instillation via intratracheal intubation, with a 40 μl inoculum containing approximately $10^6$ to $10^7$ $\log_{10}$ CFU (colony forming units) of Strep. pneumoniae and are allowed to recover. Therapy is initiated 12 h after infection and continued for a total of three days. Surviving animals are killed on day 4 after infection. The lungs of all animals are homogenized and processed to determine bacterial load, that is expected to be substantially reduced in the treatment group receiving the formulations of the invention, in comparison with the untreated control.

The results reported above show that the formulations of the invention are in general well tolerated, in particular at the injection site, as demonstrated by the absence of necrotic inflammation and urine discoloration.

The results indicate that the delivered drug is effective in treating infections caused also by multiresistant microorganisms.

The formulations of the invention therefore can be effectively administered to a patient in need thereof to control or cure infections sustained by microorganisms that are known to be susceptible to ramoplanin or an antibiotic of the ramoplanin family.

Particularly preferred is the use of the formulations of the invention in antibiotic treatment of serious Gram positive infections such as bacteremia, endocarditis and pneumonia. In particular the use of the formulations of the invention is expecially suitable for systemic treatment of severe infections caused by Gram positive resistant or multiresistant microorganisms, such as coagulase-positive and negative staphylococci, penicillin resistant streptococci or glycopeptide resistant enterococci.

In the present disclosure, the term "patient" is intended to refer to warm blooded animals such as rodents, felines, equines, bovids, and primates, including humans. Preferred as "patients" according to the invention, in addition to humans, are pet and farm animals.

An example of dosage range of ramoplanin or a member of the ramoplanin family that can be administered through formulation of the invention, that is predicted to be effective for human therapy, is preferably between 0.5 and 1 g/die, while a preferred formulation contains about between 1 and 20 mg/ml, preferably, between 1.5 and 15 mg/ml, most preferably between about 3 to about 5 mg/ml of ramoplanin or a member of ramoplanin family.

Particularly preferred is the use of the formulations of the invention in severe enterococcal infections, particularly those attributable to vancomycin-resistant strains, for which no really effective treatment is currently available (see for instance M. B. Edmond et al., Clinical Infectious Diseases, 1996; 23: 1234–1239) as well as infections wherein penicillin-resistant streptococci are present.

In such treatments, the formulation of the invention is preferably employed as a slow infusion by a central vein.

The formulations of the invention are prepared according to the conventional techniques, on the basis of the present disclosure. The pH of the final preparation is lower than 7 and preferably between 4 and 6.5, with a pH between 5.5 and 6.5 being currently most preferred.

If necessary the pH of the final formulation is adjusted to the desired value by the known procedures.

The ramoplanin (or a member of ramoplanin family) i.v. formulation of this invention can be in the form of a ready to use dosage form containing both the antibiotic and the fat emulsion product or can be in the form of a kit comprising separate packagings or containers containing ramoplanin (or a member of ramoplanin family), and the fat emulsion product for constitution of said i.v. formulation when use is needed. In particular, said kit may consist of vials or similar containers containing the dose of lyophylized sterile antibiotic, ampuls containing water for injection in amount sufficient to dissolve the antibiotic and bottles containing the sterile fat emulsion product in amount appropriate for constituting the desired i.v. formulation.

Examples of specific formulations of the invention and formulation procedures are reported below.

TABLE V

Formulations of ramoplanin (10 mg/ml) in in varying dilutions of Intralipid ®.

| | 10% (w/vol) Intralipid (ml) | 5% Glucose (w/vol) | 50 mg/ml Ramoplanin (ml) | Intralipid ®/ Ramoplanin |
|---|---|---|---|---|
| A | 8 | — | 2 | 8% (w/vol)/ 10 mg/ml |
| B | 4 | 4 | 2 | 4% (w/vol)/ 10 mg/ml |
| C | 2 | 6 | 2 | 2% (w/vol)/ 10 mg/ml |

Operatively, to 10% Intralipid® (Pharmacia), under moderate stirring, the glucose solution is slowly added followed by the ramoplanin solution.

The solution of ramoplanin in distilled water is prepared by dissolving 562 mg of ramoplanin (89% potency determined by a HPLC assay) in distilled water (5 ml) and then bringing to the final volume (10 ml).

TABLE VI

Formulations of ramoplanin (1 mg/ml) in in varying dilutions of Intralipid ®.

| | 10% (w/vol) Intralipid (ml) | 0.9% Saline (w/vol) | 10 mg/ml Ramoplanin (ml) | Intralipid ®/ Ramoplanin |
|---|---|---|---|---|
| D | 9 | — | 1 | 9% / 1 mg/ml |
| E | 1 | 8 | 1 | 1% / 1 mg/ml |
| F | 0.5 | 8.5 | 1 | 0.5% / 1 mg/ml |
| G | 0.2 | 8.8 | 1 | 0.2% / 1 mg/ml |

A solution of ramoplanin at 10 mg/ml of activity was prepared in NaCl 0.9% (w/vol). The solution was sterilized by filtration with 0.22 μm pore-size filters.

1 ml of the ramoplanin solution was added to an aliquot of Intralipid® diluted to the desired concentration by slow addition of the appropriate volume of 0.9% NaCl. The mixture was vigorously shaken to obtain a homogeneous dissolution in the fat emulsion.

What is claimed is:

1. A pharmaceutical formulation for intravenous administration which comprises ramoplanin or a member of the ramoplanin family of formula I

FORMULA I

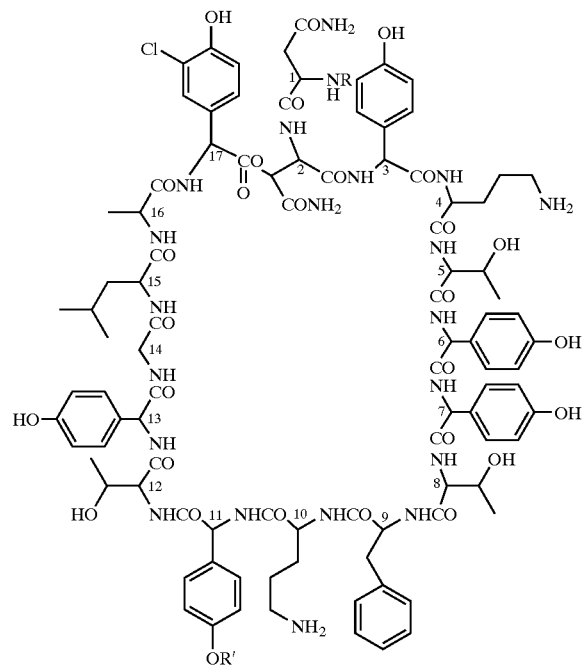

Wherein:
R represents —CO—CH=CH—CH=CH—CH$_2$— CH$_2$—CH$_3$,
—CO—CH=CH—CH=CH—CH$_2$—CH (CH$_3$)$_2$,
—CO—CH=CH—CH=CH—CH$_2$—CH$_2$—CH (CH$_3$)$_2$,
—CO—CH$_2$—CH$_2$—CH$_2$—CH$_2$—CH$_2$—CH$_2$— CH$_3$, —CO—CH$_2$—CH$_2$—CH$_2$—CH$_2$—CH$_2$—CH (CH$_3$)$_2$
or
—CO—CH$_2$—CH$_2$—CH$_2$—CH$_2$—CH$_2$—CH$_2$—CH (CH$_3$)$_2$ R' represents alpha-D-mannopyranosyl or 2-O-alpha-D-mannopyranosyl-alpha-D-mannopyranosil, or R' represents 2,3-O-di[alpha-D-mannopyranosyl]-D-mannopyranosyl when R represents —CO—CH=CH—CH=CH—CH$_2$—CH(CH$_3$)$_2$, a pharmaceutically acceptable acid addition salt thereof, or a mixture thereof in any proportion, in admixture with an amount of fat emulsion product for intravenous administration being a lipid in water microemulsion suitable to be administered by the parental route comprising an oil phase, an emulsifier, and at least one additive as an osmotic agent wherein the concentration of the oil phase is from 0.2% to 40% (weight/vol) in the final intravenous formulation and comprises at least one vegetal oil consisting of soybean oil, cottonseed oil and sunflower oil which are partially or totally substituted with a mixture of long chain fatty acids in the form of triglycerides having a percent (wt/wt) composition substantially similar to that of the vegetal oil, and the emulsifier is based on at least one phospholipid.

2. A formulation according to claim 1 wherein the fat emulsion product employed for the preparation of said formulation contains from 2 to 40 percent, (weight/vol), of oil phase, from 0.2 to 5 percent, (weight/vol), of emulsifier and an additive in an amount suitable to control osmolarity.

3. A formulation according to claim 1 wherein the oil phase contains long chain fatty acids in the form of triglycerides in the following proportions by weight:

linoleic acid 40–70% oleic acid 15–30% palmitic acid 5–15% linoleic acid 3–12% stearic acid 2–6% wherein the % is wt% based on the total fatty acid content and the total proportions are selected to add up to 100%.

4. A formulation according to claim 1 wherein the fat emulsion product employed for the preparation of said formulation comprises a composition selected from those reported in the following tables:

|  | Fat emulsion product 1 | Fat emulsion product 2 | Fat emulsion product 3 |
| --- | --- | --- | --- |
| Soybean oil (w/vol) | 10% | 20% | 5% |
| Safflower oil (w/vol) | — | — | 5% |
| Egg yolk phospholipids (w/vol) | 1.2% | 1.2% | 1.2% |
| Glycerol (w/vol) | 2.25% | 2.25% | 2.5% |
| Fatty acids composition of vegetable oils (w/vol) |  |  |  |
| Linoleic acid | 50% | 50% | 65.8% |
| Oleic acid | 26% | 26% | 17.7% |
| Palmitic acid | 10% | 10% | 8.8% |
| Linolenic acid | 9% | 9% | 4.2% |
| Stearic acid | 3.5% | 3.5% | 3.4% |
| Osmolarity (mOsm/L) | 260 | 268 | 276 |
| Approximate pH | 8 | 8 | 8 |
| Fat particle size (μm) | 0.5 | 0.5 | 0.4 |
| Caloric value (cal/ml) | 1.1 | 2.0 | 1.1 |
| Size (ml) | 50, 100 250 or 500 | 50, 100 250 or 500 | 25, 50 100, 200 Or 500 |

5. A formulation according to claim 3 wherein soybean oil and/or cottonseed oil and/or safflower oil are totally or partially replaced by a mixture of long chain fatty acids in the form of triglycerides to form a composition wherein said fatty acids are present in the respective proportions indicated in said claims and, optionally part of the above oils of long chain fatty acids is substituted by medium chain (C$_4$–C$_{12}$) triglycerides.

6. A formulation according to claim 1 wherein the concentration of the oil phase is between 4 and 25% (weight/vol) of the final formulation.

7. A formulation according to claim 1 wherein the concentration of the oil phase is between 8 and 10% (w/vol) of the final formulation.

8. A formulation according to claim 1 wherein ramoplanin is present at a concentration between 1 and 20 mg/ml.

9. A formulation according to claim 1 wherein the pH of the final formulation is lower than 8.

10. A formulation according to claim 1 wherein the pH of the final formulation is between 4 and 6.5.

11. A formulation according to claim 1 for treatment of infections caused by bacteria whose proliferation is inhibited, reduced, alleviated, or arrested in the presence of ramoplanin or a member of the ramoplanin family.

12. A method of treating at least one Gram positive infection, comprising administering the formulation according to claim 1 to a patient in need thereof.

13. A formulation according to claim 1 for
the treatment of severe infections caused by Gram positive drug-resistant or multiresistant microorganisms such as coagulase positive and negative staphylocoocly, penicillin-resistant streptococci or glycopeptide resistant enterococci.

14. A formulation according to claim 1
wherein ramoplanin factor A$_2$ is present in an amount of at least 75%.

15. A pharmaceutical composition which consists of a ready to use dosage form or of a kit comprising separate packagings or containers containing ramoplanin or a member of ramoplanin family and the fat emulsion product for constitution of a formulation according to claim 1.

16. The formulation according to claim 1, wherein said vegetal oil are selected from the group consisting of soybean oil, cottonseed oil, safflower oil and mixtures thereof.

17. The formulation to claim 1, wherein said phospholipids are from an egg source.

18. The formulation to claim 17, wherein said phospholipids are selected from the group consisting of egg lecithin, soybean lecithin, and mixtures thereof.

19. The formulation to claim 1, wherein said osmotic agent is selected form the group consisting of sorbitol, glycerol, xylitol and mixtures thereof.

20. The formulation to claim 1, wherein the oil phase is in the range of from 4 to 25 percent of the final formulation.

21. The formulation to claim 1, wherein the oil phase is in the range 8 to 18 percent of the final formulation.

22. The formulation to claim 1, wherein the oil phase is in the range of from 8 to 10 percent of the final formulation.

23. The formulation to claim 2, wherein the fat emulsion product contains form 5 to 25 percent of the oil phase.

24. The formulation to claim 2, wherein the fat emulsion product contains from 7 to 30 percent of the oil phase.

25. The formulation to claim 2, wherein the fat emulsion product contains from 0.6 to 2 percent of the emulsifier.

26. The formulation to claim 2, wherein the additive is in an amount from 1.5 to 5 percent.

27. The formulation to claim 2, wherein the additive is in an amount from 2 to 3 percent.

28. The formulation to claim 6, wherein the concentration of the oil phase is from 8 to 18 percent of the final formulation.

29. The formulation to claim 8, wherein the ramoplanin is present in a concentration of from 1.5 to 15 mg/ml.

30. The formulation to claim 8, wherein the ramoplanin is present in a concentration of from 3 to 5 mg/ml.

31. The formulation to claim 9, wherein the pH of the final formulation is lower than 7.

32. The formulation to claim 1, wherein the member of the ramoplanin family of formula I is factor $A_2$.

33. The formulation to claim 1, wherein the member of the ramoplanin family of formula I is factor $A_2$.

34. The formulation to claim 1, wherein the member of the ramoplanin family of formula I is factor $A_2$.

35. The formulation to claim 1, wherein the member of the ramoplanin family of formula I is factor $A_2$.

36. The formulation to claim 1, wherein the member of the ramoplanin family of formula I us factor $A_2$.

37. The formulation to claim 2, wherein the member of the ramoplanin family of formula I is factor $A_2$.

38. The method according to claim 12, wherein the at least one Gram positive infection is at least one member selected from the group consisting of bacteremia, endocarditis, and pneumonia.

39. The formulation to claim 1, wherein the phospholipids emulsifier is based on phospholipid from and egg source.

40. The formulation to claim 1, wherein the phospholipid emulsifier is based on a phospholipid selected from egg lecithin, soybean lecithin, or a mixture thereof.

41. The formulation to claim 1, wherein the osmotic agent is at least one member selected from the group consisting of sorbitol, glycerol, and xylitol.

42. The formulation to claim 1, wherein the oil phase is present in an amount ranging from 4 to 25% wt/vol of the final formulation.

43. The formulation to claim 1, wherein the oil phase is present in an amount ranging from 8 to 18% wt/vol of the final formulation.

44. The formulation to claim 1, wherein the oil phase is present in an amount ranging from 8 to 10% wt/vol of the final formulation.

* * * * *